US008008461B2

(12) United States Patent
Kizaki et al.

(10) Patent No.: US 8,008,461 B2
(45) Date of Patent: Aug. 30, 2011

(54) CARBONYL REDUCTASE, GENE THEREFOR AND USE THEREOF

(75) Inventors: Noriyuki Kizaki, Takasago (JP); Makoto Ueda, Takasago (JP); Daisuke Moriyama, Takasago (JP); Naoaki Taoka, Takasago (JP); Yoshihiko Yasohara, Takasago (JP)

(73) Assignee: Kaneka Corporation, Osaka (JP)

( * ) Notice: Subject to any disclaimer, the term of this patent is extended or adjusted under 35 U.S.C. 154(b) by 148 days.

(21) Appl. No.: 11/665,065

(22) PCT Filed: Oct. 20, 2005

(86) PCT No.: PCT/JP2005/019269
§ 371 (c)(1),
(2), (4) Date: Apr. 11, 2007

(87) PCT Pub. No.: WO2006/046455
PCT Pub. Date: May 4, 2006

(65) Prior Publication Data
US 2009/0029430 A1 Jan. 29, 2009

(30) Foreign Application Priority Data
Oct. 27, 2004 (JP) ................. 2004-312365

(51) Int. Cl.
*C07H 21/04* (2006.01)
*C12N 9/02* (2006.01)
*C12P 21/02* (2006.01)
*C12P 13/00* (2006.01)
*C07C 255/01* (2006.01)

(52) U.S. Cl. ...... 536/23.2; 435/189; 435/69.1; 435/128; 558/410

(58) Field of Classification Search ............... 536/23.2; 435/189, 128, 69.1; 558/410
See application file for complete search history.

(56) References Cited

U.S. PATENT DOCUMENTS
6,083,752 A 7/2000 Ikenaka et al.
6,645,746 B1 * 11/2003 Kizaki et al. ............ 435/189

FOREIGN PATENT DOCUMENTS
EP 0 967 271 A1 12/1999
EP 1 1520 54 A1 11/2001
EP 1 505 155 A1 2/2005
WO WO 98/35025 A1 8/1998
(Continued)

OTHER PUBLICATIONS

Current Protocols in Molecular Biology, Hybridization Analysis of DNA Blots, Chapter 2.10, 1993.*

(Continued)

*Primary Examiner* — Karen Cochrane Carlson
*Assistant Examiner* — Rosanne Kosson
(74) *Attorney, Agent, or Firm* — Sughrue Mion, PLLC (57) ABSTRACT

The present invention is to provide a process for efficiently producing an optically active alcohol including (R)-3-hydroxy-3-phenylpropanenitrile. One of the features of the present invention is a polypeptide having an activity of asymmetrically reducing 3-oxo-3-phenylpropanenitrile isolated from a microorganism belonging to the genus *Candida* to produce (R)-3-hydroxy-3-phenylpropanenitrile, DNA encoding the polypeptide and a transformant of producing the polypeptide. Another feature of the present invention is a process for producing an optically active alcohol such as (R)-3-hydroxy-3-phenylpropanenitrile by reducing a carbonyl compound such as 3-oxo-3-phenylpropanenitrile by use of the polypeptide or the transformant.

11 Claims, 1 Drawing Sheet

FOREIGN PATENT DOCUMENTS

| WO | WO 01/40450 A1 | 6/2001 |
| WO | WO 03093477 A1 | 11/2003 |

OTHER PUBLICATIONS

Alignment of Seq ID No. 2 with Seq ID No. 1 of Kizaki et al. (US 6,645,746), http://blast.ncbi.nlm.nih.gov/Blast.cgi, performed on NCBI Blast web site Mar. 6, 2009.*

Result 1, search in issued patents polynucleotide database, alignment of instant Seq ID No. 1 with Kizaki et al., US 6,645,746 B1, Seq ID No. 2, performed on May 7, 2009.*

H. Guo et al., "Protein Tolerance to Random Amino Acid Change", PNAS 101(25):9205-9210, 2004.*

Score search results 2-6, search in Geneseq protein database, alignment of instant Seq ID No. 2 with a sequence of each cited reference, performed on Mar. 3, 2009, 7 pages.*

Y. Yasohara et al., "Stereoselective reduction of alkyl 3-oxobutanoate by carbonyl reductase from *Candida magnoliae*",Tetrahedron: Asymmetry, 2001, p. 1713-1718, vol. 12.

J.R. Dehli et al., "Enantio- and chemoselective bioreduction of β-keto nitriles by the fungus *Curivularia lunata*", Tetrahedron: Asymmetry, 2000, p. 3693-3700, vol. 11.

* cited by examiner

[Figure 1]

```
SEQUENCE LISTING

<160> NUMBER OF SEQ ID NOS: 9

<210> SEQ ID NO 1
<211> LENGTH: 723
<212> TYPE: DNA
<213> ORGANISM: Candida magnoliae

<400> SEQUENCE: 1
atgtcttctc ttcacgctct tgttacaggt gctagccgcg gtattggcga ggcctcggcc      60
attaagctcg cccaagaggg ctacagcgtc acgctcgcgt cgcgcggtgt cgacaagctg     120
aacgaggtga aggccaagct tcctgttgtg aagcagggcc aggagcacta cgtctggccg     180
cttgatctca gcgatgtgca ggcggcgctc gagttcaagg gcgcgccgct gcccgcgagc     240
aagtacgacc tgtttgtttg caacgccggc gtcgcctcga tgtcgccgac tgccgaccac     300 gatgacgcg actggcagca cattctgacc gtgaaccttt cgagcccgat tgcgctcacg     360
aagacgctcg tgaaggcggt aggcgagcgg cccaaggaca agccgttcca catcgtgtac     420
atctcttcgg tggttagccg ccgcggcttc gcgggcgctg cggtgtacag cgcgtcgaag     480
gctggtctcg acggctttgc gcgctcgatt gcccgcgagc tcgcccgaa gggaatccat      540 gtgaactctg tgcagcctgg tctcacgaag accgagatga caaccagctt cgatcctccg     600
gccgatctgc ccatcagcgg atggatctac ccggatgcaa ttgccgatgc cgtggtgttc     660
ttcgccaagt cgacgaacgt cacaggtgcg aacatcatcg tcgacaatgg ctctaccgtt     720
taa                                                                   723

<210> SEQ ID NO 2
<211> LENGTH: 240
```

```
<212> TYPE: PRT
<213> ORGANISM: Candida magnoliae

<400> SEQUENCE: 2

Met Ser Ser Leu His Ala Leu Val Thr Gly Ala Ser Arg Gly Ile Gly
 1               5                  10                  15

Glu Ala Ser Ala Ile Lys Leu Ala Gln Glu Gly Tyr Ser Val Thr Leu
                20                  25                  30

Ala Ser Arg Gly Val Asp Lys Leu Asn Glu Val Lys Ala Lys Leu Pro
            35                  40                  45

Val Val Lys Gln Gly Gln Glu His Tyr Val Trp Pro Leu Asp Leu Ser
    50                  55                  60

Asp Val Gln Ala Ala Leu Glu Phe Lys Gly Ala Pro Leu Pro Ala Ser
65                  70                  75                  80

Lys Tyr Asp Leu Phe Val Cys Asn Ala Gly Val Ala Ser Met Ser Pro
                85                  90                  95

Thr Ala Asp His Asp Asp Ala Asp Trp Gln His Ile Leu Thr Val Asn
               100                 105                 110

Leu Ser Ser Pro Ile Ala Leu Thr Lys Thr Leu Val Lys Ala Val Gly
           115                 120                 125

Glu Arg Pro Lys Asp Lys Pro Phe His Ile Val Tyr Ile Ser Ser Val
       130                 135                 140

Val Ser Arg Arg Gly Phe Ala Gly Ala Ala Val Tyr Ser Ala Ser Lys
145                 150                 155                 160

Ala Gly Leu Asp Gly Phe Ala Arg Ser Ile Ala Arg Glu Leu Gly Pro
               165                 170                 175

Lys Gly Ile His Val Asn Ser Val Gln Pro Gly Leu Thr Lys Thr Glu
           180                 185                 190

Met Thr Thr Ser Phe Asp Pro Pro Ala Asp Leu Pro Ile Ser Gly Trp
       195                 200                 205

Ile Tyr Pro Asp Ala Ile Ala Asp Ala Val Val Phe Phe Ala Lys Ser
   210                 215                 220

Thr Asn Val Thr Gly Ala Asn Ile Ile Val Asp Asn Gly Ser Thr Val
225                 230                 235                 240

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)
<223> OTHER INFORMATION: A, T, C, or G

<400> SEQUENCE: 3
cargarcayt aygtntggcc                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: A, T, C or G
```

```
<400> SEQUENCE: 4
atygcrtcng grtadatcca                                            20

<210> SEQ ID NO 5
<211> LENGTH: 442
<212> TYPE: DNA
<213> ORGANISM: Candida magnoliae

<400> SEQUENCE: 5
gcttgatctc agcgatgtgc aggcggcgct cgagttcaag ggcgcgccgc tgcccgcgag    60
caagtacgac ctgtttgttt gcaacgccgg cgtcgcctcg atgtcgccga ctgccgacca   120
cgatgacgcg gactggcagc acattctgac cgtgaacctt tcgagcccga ttgcgctcac   180
gaagacgctc gtgaaggcgg taggcgagcg gcccaaggac aagccgttcc acatcgtgta   240
catctcttcg gtggttagcc gccgcggctt cgcgggcgct gcggtgtaca gcgcgtcgaa   300
ggctggtctc gacggctttg cgcgctcgat tgcccgcgag ctcggcccga agggaatcca   360
tgtgaactct gtgcagcctg gtctcacgaa gaccgagatg acaaccagct tcgatcctcc   420
ggccgatctg cccatcagcg ga                                          442

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcatatgt cttctcttca cgctcttg                                    28

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcgaattct tattaaacgg tagagccatt gtcg                             34

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccgaattct aaggaggtta acaatgtata aa                               32

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggtcgact tatccgcgtc ctgcttgg                                    28
```

CARBONYL REDUCTASE, GENE THEREFOR AND USE THEREOF

This application is a National Stage of International Application No. PCT/JP2005/019269, filed on Oct. 20, 2005, claiming priority based on Japanese Patent Application No. 2004-312365, filed Oct. 27, 2004, the contents of which are incorporated herein by reference in their entirety.

TECHNICAL FIELD

The present invention relates to a polypeptide (carbonyl reductase) having an activity of asymmetrically reducing 3-oxo-3-phenylpropanenitrile represented by the formula (1) below:

[Chemical formula 9]

(1)

to produce (R)-3-hydroxy-3-phenylpropanenitrile represented by the formula (2) below:

[Chemical formula 10]

(2)

and isolated from a microorganism having said activity; DNA encoding the polypeptide; a vector containing the DNA; and a transformant transformed with the vector.

The present invention also relates to a process for producing an optically active alcohol, in particular, (R)-3-hydroxy-3-phenylpropanenitrile represented by the formula (2) above using the polypeptide or the transformant.

(R)-3-hydroxy-3-phenylpropanenitrile is a useful compound as an intermediate of a pharmaceutical product such as a β-adrenaline receptor blocker.

BACKGROUND ART

As a process for producing optically active 3-hydroxy-3-phenylpropanenitrile, there are known 1) a process for deriving it from an optically active precursor substance (Patent Documents 1 and 2); 2) a process for optically resolving racemic 3-hydroxy-3-phenylpropanenitrile with a hydrolyzing enzyme such as lipase (Patent Document 3, Non-Patent Document 2); 3) a process for condensing benzaldehyde and acetonitrile in the presence of an asymmetric ligand and a metallic catalyst (Non-patent document 3); 4) a process for reducing an carbonyl group of 3-oxo-3-phenylpropanenitrile in the presence of an asymmetric ligand or an asymmetric catalyst (Patent Document 4 and Non-Patent Document 4); and 5) a process for reducing an carbonyl group of 3-oxo-3-phenylpropanenitrile by use of a microorganism (Non-Patent Documents 5 and 6).

Non-Patent Document 1: Bulletin of the Korean Chemical Society, 23, 1693 (2002)
Non-Patent Document 2: Advanced Synthesis & Catalysis, 344, 947 (2002)
Non-Patent Document 3: Organic Letters, 5, 3147 (2003)
Non-Patent Document 4: Tetrahedron: Asymmetry, 3, 677 (1992)
Non-Patent Document 5: Tetrahedron: Asymmetry, 11, 3693 (2000)
Non-Patent Document 6: Organic Letters, 1, 1879 (1999)
Patent Document 1: US. Patent Application Laid-Open No. 2004/110985
Patent Document 2: Japanese Patent Application Laid-Open No. 5-92946
Patent Document 3: National Publication of International Patent Application No. 2004-520039
Patent Document 4: Japanese Patent Application Laid-Open No. 2003-201269

BRIEF SUMMARY OF THE INVENTION

The processes disclosed in the aforementioned documents individually have drawbacks. In the process 1), an expensive precursor substance is required. In the process 2), since a theoretical yield is 50%, a half of a raw material is wasted. In the processes 3) and 4), an expensive asymmetric ligand or asymmetric catalyst is required. In the process 5), a productivity per reaction volume is low. Any one of these processes is far from an economic process.

In view of the aforementioned circumstances, an object of the present invention is to provide a useful polypeptide in producing (R)-3-hydroxy-3-phenylpropanenitrile, DNA encoding the polypeptide, a vector containing the DNA, and a transformant transformed with the vector.

Another object of the present invention is to provide processes for effectively producing various types of optically active alcohols including (R)-3-hydroxy-3-phenylpropanenitrile, by use of the polypeptide and the transformant.

The present inventors isolated a polypeptide having an activity of asymmetrically reducing 3-oxo-3-phenylpropanenitrile to produce (R)-3-hydroxy-3-phenylpropanenitrile from a microorganism having the activity. Furthermore, they isolated DNA encoding the polypeptide and succeeded in creating a transformant capable of producing the polypeptide by using the DNA in high yield. Moreover, they found that various types of useful optically active alcohols including (R)-3-hydroxy-3-phenylpropanenitrile can be efficiently produced by use of the polypeptide or the transformant. Based on these, the present invention was accomplished.

More specifically, one of the features of the present invention is a polypeptide having an activity of asymmetrically reducing 3-oxo-3-phenylpropanenitrile to produce (R)-3-hydroxy-3-phenylpropanenitrile. Another feature of the present invention is DNA encoding the polypeptide. Still another feature of the present invention is a vector containing the DNA. A further feature of the present invention is a transformant containing the vector. Still a further feature of the present invention is a process for producing an optically active alcohol including (R)-3-hydroxy-3-phenylpropanenitrile, by use of the polypeptide or the transformant.

The present invention can provide a practical process for producing a useful and optically active alcohol including (R)-3-hydroxy-3-phenylpropanenitrile.

DETAILED DESCRIPTION OF THE INVENTION

The present invention will be more specifically explained below.

Gene manipulation such as isolation of DNA, preparation of a vector, and formation of a transformant can be performed in accordance with the method described in publications such as Molecular Cloning 2nd Edition (Cold Spring Harbor Laboratory Press, 1989), unless otherwise specified. Furthermore, the reference symbol "%" used in the description of the specification refers to % (w/v), unless otherwise specified.

1. Polypeptide and its Source

The polypeptide of the present invention is one having an activity of asymmetrically reducing 3-oxo-3-phenylpropanenitrile to produce (R)-3-hydroxy-3-phenylpropanenitrile. Such a polypeptide can be isolated from a microorganism having the activity. The microorganism from which the polypeptide of the present invention is derived is not particularly limited. For example, yeast belonging to the genus *Candida* may be mentioned. Particularly preferably, *Candida magnoliae* strain NBRC0661 may be mentioned. The microorganism is available from an independent organization, the National Institute of Technology and Evaluation, Biological Resource Center (NBRC, 2-5-8 Kazusakamatari, Kisarazu-shi, Chiba, 292-0818, JAPAN).

As a medium for culturing a microorganism from which the polypeptide of the present invention is derived, any liquid nutrition medium generally used and containing a carbon source, nitrogen source, inorganic salts, and organic nutrients, etc., can be used as long as the microorganism can be proliferated in the medium.

2. Isolation of Polypeptide

Isolation of the polypeptide of the present invention from a microorganism from which the polypeptide is derived can be generally performed by using known protein purification methods in appropriate combination, for example, as described below. First, the microorganism is cultured in an appropriate medium and microorganism's cells are collected from the culture solution by centrifugation or filtration. The obtained cells are disrupted by an ultrasonic homogenizer or a physical means using glass beads, and thereafter, cell residues are centrifugally removed to obtain a cell-free extract. Subsequently, the cell-free extract is subjected to a process such as salting-out (e.g., precipitation with ammonium sulfate and precipitation with sodium phosphate, etc.), precipitation with a solvent (precipitation of a protein fraction by acetone, ethanol or the like), dialysis, gel filtration chromatography, ion exchange chromatography, reversed-phase chromatography, and ultrafiltration, singly or in combination. In this manner, the polypeptide of the present invention is isolated from the cell-free extract.

3. Reduction Reaction

The activity of reducing 3-oxo-3-phenylpropanenitrile can be determined, for example, by adding a 0.5 mM 3-oxo-3-phenylpropanenitrile as a substrate, 0.25 mM coenzyme NADPH and a crude enzyme to a 100 mM phosphate buffer (pH 6.5) containing 0.33% (v/v) dimethylsulfoxide, allowing the mixture to react at 30° C. for one minute, measuring absorbance of the resultant reaction solution at a wavelength of 340 nm, and calculating the activity from the reduction rate of the absorbance.

The optical purity of 3-hydroxy-3-phenylpropanenitrile produced in the aforementioned reaction can be measured by capillary gas chromatography (column: CHIRALDEX G-TA manufactured by Tokyo Chemical Industry Co., Ltd., φ 0.25 mm×20 m, column temperature: 130° C., carrier gas: helium (150 kPa), detection: FID).

4. DNA

The DNA of the present invention is one encoding the polypeptide of the present invention mentioned above. Any DNA may be used as long as it can express the polypeptide in a host cell to which the DNA is introduced in accordance with a method as described later. The DNA may optionally contain a non-translation region. As long as the polypeptide can be obtained, one skilled in the art can obtain such DNA from a microorganism from which the polypeptide is derived, in accordance with a known method, for example, the method set forth below.

First, the isolated polypeptide of the present invention is digested with an appropriate endopeptidase. The resultant peptide fragments are separated by reverse-phase HPLC. Subsequently, the whole or part of amino acid sequences of these peptide fragments are determined, for example, by an ABI492-type protein sequencer (manufactured by Applied Biosystems).

Based on the amino acid sequence data thus obtained, a PCR (Polymerase Chain Reaction) primer is synthesized for amplifying a part of DNA encoding the polypeptide. Subsequently, the chromosomal DNA of a microorganism from which the polypeptide is derived is prepared by a general DNA isolation method, for example, a method of Vissers et al. (Appl. Microbiol. Biotechnol., 53, 415 (2000)). PCR is performed using the chromosomal DNA as a template and the PCR primer described above to amplify a part of the DNA encoding the polypeptide and the base sequence thereof is determined. The determination of the base sequence can be performed for example, by an ABI373-type DNA Sequencer (manufactured by Applied Biosystems).

When a part of DNA encoding the polypeptide is clarified, the whole sequence of the DNA can be determined by use of, for example, i-PCR method (Nucl. Acids Res., 16, 8186 (1988)).

As an example of DNA of the present invention thus obtained, mention may be made of DNA containing a base sequence represented by SEQ ID NO: 1 of the sequence listing. Furthermore, DNA that is hybridized, under stringent conditions, with the DNA having a base sequence represented by SEQ ID NO: 1 of the sequence listing and a complementary base sequence thereof and that is encoding a polypeptide having an activity of asymmetrically reducing 3-oxo-3-phenylpropanenitrile to produce (R)-3-hydroxy-3-phenylpropanenitrile may be also included in the DNA of the present invention.

DNA that is hybridized, under stringent conditions, with the DNA having a base sequence represented by SEQ ID NO: 1 of the sequence listing and a complementary base sequence thereof refers to one that specifically forms a hybrid with the DNA having a base sequence represented by SEQ ID NO: 1 of the sequence listing and a complementary base sequence thereof when a colony hybridization method, plaque hybridization method, Southern hybridization method or the like is performed.

The stringent conditions herein refer to those in which hybridization is performed at 65° C. in an aqueous solution having a composition of 75 mM trisodium citrate, 750 mM sodium chloride, 0.5% sodium dodecyl sulfate, 0.1% bovine serum albumin, 0.1% polyvinylpyrrolidone and 0.1% Ficoll 400 (manufactured by Amersham Bioscience), followed by washing with an aqueous solution having a composition of 15 mM trisodium citrate, 150 mM sodium chloride, and 0.1% sodium dodecyl sulfate at 60° C. Preferably, after hybridization is performed in the aforementioned conditions, washing is performed by use of an aqueous solution having a composition of 15 mM trisodium citrate, 150 mM sodium chloride, and 0.1% sodium dodecyl sulfate, at 65° C., and more preferably, washing is performed with an aqueous solution containing 1.5 mM trisodium citrate, 15 mM sodium chloride, and 0.1% sodium dodecyl sulfate, at 65° C.

5. Polypeptide

As an example of the polypeptide of the present invention, mention can be made of a polypeptide consisting of the amino acid sequence represented by SEQ ID NO: 2 of the sequence listing and encoded by the base sequence represented by SEQ ID NO: 1 of the sequence listing.

Furthermore, the polypeptide having a homology of not less than a certain value with the polypeptide consisting of the amino acid sequence represented by SEQ ID NO: 2 of the sequence listing, and having an activity of asymmetrically reducing 3-oxo-3-phenylpropanenitrile to produce (R)-3-hydroxy-3-phenylpropanenitrile is functionally equivalent to the polypeptide and included in the present invention.

The homology of the sequence herein is expressed, for example, by an identity value relative to the entire sequence when two amino acid sequences are analyzed and compared by a homology search program FASTA (W. R. Pearson & D. J. Lipman P.N.A.S. (1988) 85:2444-2448). As a polypeptide equivalent to that consisting of the amino acid sequence represented by SEC) ID NO: 2 of the sequence listing, mention may be made of a polypeptide having a homology of 70% or more to the polypeptide, preferably 80% or more, and more preferably 90% or more.

Such a polypeptide can be obtained by, for example, ligating DNA, which hybridizes, under stringent conditions, with the DNA having a base sequence represented by SEQ ID NO: 1 of the sequence listing and a complementary base sequence thereof as previously described, to an appropriate vector, introducing into an appropriate host cell, and expressing the vector. Alternatively, such a polypeptide can be also obtained by processing the polypeptide consisting of amino acid sequence represented by SEQ ID NO: 2 of the sequence listing to substitute, insert, delete or add an amino acid(s) in accordance with known methods described, for example, in Current Protocols in Molecular Biology (John Wiley and Sons, Inc., 1989). The number of amino acids to be replaced, inserted, deleted or added in the aforementioned polypeptide is not particularly limited as long as the activity of asymmetrically reducing 3-oxo-3-phenylpropanenitrile to produce (R)-3-hydroxy-3-phenylpropanenitrile is not significantly decreased; however, the number of amino acids is 20 amino acids or less, preferably 5 or less, and further preferably 2 or 1.

6. Vector and Transformant

The vector for use in introducing the DNA of the present invention into a microbial host and expressing the DNA introduced in the microbial host is not particularly limited as long as the gene encoded by the DNA can be expressed in an appropriate microbial host. Examples of such a vector include a plasmid vector, phage vector and cosmid vector. Besides these, a shuttle vector capable of exchanging a gene with another host strain may be used.

Such a vector generally contains regulators such as lac UV5 promoter, trp promoter, trc promoter, tac promoter, lpp promoter, tufB promoter, recA promoter, and pL promoter and can be suitably used as an expression vector containing an expression unit operably linked with the DNA of the present invention. For example, pUCNT (U.S. Pat. No. 6,083,752) can be suitably used.

The term "regulatory element" used in the specification refers to a base sequence having a functional promoter and any of transcription elements (such as an enhancer, CCAAT box, TATA box, and SPI site).

The term "operably linked" used in the specification means that various regulatory elements such as a promoter and an enhancer for regulating the expression of a gene are ligated to the gene in a functional state in a host cell. It is known to one skilled in the art that the type and kind of regulatory element may vary depending upon the host.

Examples of the expression vector of the present invention include pNTCM (described later) having the DNA represented by SEQ ID NO: 1 introduced in pUCNT.

As a host cell to which a vector containing the DNA of the present invention is introduced, mention may be made of bacterial cells, yeasts, fungi, vegetable cells and animal cells. In view of introduction and expression efficiencies, bacterial cells, in particular, *Escherichia coli*, is preferable. The vector containing the DNA of the present invention can be introduced into a host cell by a known method. When *E. coli* is used as a host cell, the vector can be introduced into the host cell by using, for example, a commercially available *E. coli* HB101 competent cell (manufactured by Takara Bid Inc.).

As an example of a transformant according to the present invention, mention may be made of *E. coli* HB101 (pNTCM) FERM BP-10418 (described later). The transformant has been deposited as of Sep. 26, 2005 under the aforementioned accession number with an independent organization, the International Patent Organism Depositary of the National Institute of Advanced Industrial Science and Technology (located at Tsukuba Central 6, 1-1-1 Higashi, Tsukuba, Ibaraki, 305-8566, Japan). Note that the original national deposition date of Oct. 23, 2003 for the strain has been transferred to international deposition based on the Budapest Treaty.

7. Polypeptide Having a Coenzyme Regeneration Activity

When the polypeptide of the present invention is reacted in contact with a compound having a carbonyl group and a coenzyme such as NADPH, it asymmetrically reduces the compound having a carbonyl group to produce an optically active alcohol. At this time, as the reaction proceeds, a coenzyme such as NADPH is converted into an oxidation type. However, when the reaction of the polypeptide of the present invention is performed in the presence of a polypeptide having an ability (hereinafter referred to as "coenzyme regeneration ability") to convert the oxidation-type coenzyme into a reduction type and the compound serves as a substrate for the polypeptide, the amount of an expensive coenzyme can be greatly reduced. Examples of the polypeptide having a coenzyme regeneration ability include hydrogenase, formic acid dehydrogenase, alcohol dehydrogenase, aldehyde dehydrogenase, glucose-6-phosphate dehydrogenase and glucose dehydrogenase. Preferably, glucose dehydrogenase may be used.

8. Use of Transformant

When a transformant containing DNA encoding the polypeptide is used in place of the polypeptide of the present invention, an optically active alcohol can be also produced. Furthermore, even if a transformant containing both DNA encoding the polypeptide of the present invention and DNA encoding the polypeptide having a coenzyme regeneration ability is used, an optically active alcohol can be also produced. In particular, when a transformant containing both DNA encoding the polypeptide of the present invention and DNA encoding the polypeptide having a coenzyme regeneration ability is used, an optically active alcohol can be produced more effectively because it is not necessary to separately prepare/add an enzyme for regenerating the coenzyme.

Note that, with respect to a transformant containing DNA encoding the polypeptide of the present invention or a transformant containing both DNA encoding the polypeptide of the present invention and DNA encoding the polypeptide having a coenzyme regeneration ability, not only cultured bacterial cells of the transformant but also a processed product of the transformant can be used to produce an optically active alcohol. The "processed product of the transformant" refers to cells treated with a surfactant and an organic solvent, dried cells, disrupted cells, crude cell-extract or a mixture thereof. Besides these, it refers to immobilized cells fixed by means of a known means such as a crosslinking method, physical adsorption method and entrapment method.

The transformant containing both DNA encoding the polypeptide of the present invention and DNA encoding the polypeptide having a coenzyme regeneration ability can be obtained by introducing both DNA encoding the polypeptide of the present invention and DNA encoding the polypeptide having a coenzyme regeneration ability into a single vector and inserting the vector to a host cell. Or it may be also obtained by introducing these two types of DNA fragments into two different types of vectors of a heterothallism group, respectively, and inserting these two types of vectors to a single host cell.

As an example of a vector into which both DNA encoding the polypeptide of the present invention and DNA encoding a polypeptide having a coenzyme regeneration ability are introduced, mention may be made of pNTCMG1 (described later), which is the aforementioned expression vector pNTCM having a glucose dehydrogenase gene derived from *Bacillus megaterium* introduced therein. Furthermore, as an example of a transformant containing both DNA encoding the polypeptide of the present invention and DNA encoding a polypeptide having a coenzyme regeneration ability, mention may be made of *E. coli* HB101 (pNTCMG1) (described later) obtained by transforming *E. coli* HB101 with the vector.

Culturing a transformant containing DNA encoding the polypeptide of the present invention and a transformant containing both DNA encoding the polypeptide of the present invention and DNA encoding the polypeptide having a coenzyme regeneration ability can be performed in a liquid nutrition medium generally used and containing a carbon source, nitrogen source, inorganic salts and organic nutrients, etc., as long as they are proliferated.

The activity of the polypeptide having a coenzyme regeneration activity in a transformant can be measured by a conventional method. For example, the activity of glucose dehydrogenase can be obtained by adding 100 mM glucose, 2 mM coenzyme NADP or NAD and an enzyme to a 1 M tris-hydrochloric acid buffer (pH 8.0) and allowing the reaction mixture to react at 25° C. for one minute, measuring absorbance at a wavelength of 340 nm, and calculating an increasing rate of the absorbance.

9. Production of Optically Active Alcohol

Production of an optically active alcohol using either the polypeptide of the present invention or a transformant containing DNA encoding the polypeptide can be performed by adding a compound containing a carbonyl group serving as a substrate, a coenzyme such as NADPH and the polypeptide of the present invention or the transformant containing DNA encoding the polypeptide to an appropriate solvent, and stirring the mixture while adjusting the pH.

On the other hand, when a reaction is performed using the polypeptide of the present invention in combination with a polypeptide having a coenzyme regeneration ability, the polypeptide having a coenzyme regeneration ability (e.g., glucose dehydrogenase) and a compound serving as a substrate thereof (e.g., glucose) are further added to the reaction composition mentioned above. Note that, also in the latter case, when the transformant containing both DNA encoding the polypeptide of the present invention and DNA encoding the polypeptide (e.g., glucose dehydrogenase) having a coenzyme regeneration ability or a processed product thereof is used, it is not necessary to separately add the polypeptide (e.g., glucose dehydrogenase) having a coenzyme regeneration ability.

The reaction may be performed in an aqueous solvent or in a mixture of an aqueous solvent and an organic solvent. Examples of the organic solvent include toluene, ethyl acetate, n-butyl acetate, hexane, isopropanol, diisopropyl ether, methanol, acetone, and dimethylsulfoxide. The reaction may be performed at a temperature of 10° C. to 70° C. and the pH of the reaction solution is maintained at 4 to 10. The reaction is performed in a batch system or a continuous system. In the case of the batch system, a reaction substrate is added in an initial concentration of 0.1% to 70% a (w/v).

10. Substrate and Product

Examples of the compound having a carbonyl group serving as a substrate, include 3-oxo-3-phenylpropanenitrile represented by, for example, the formula (1) below:

[Chemical formula 11]

(1)

ethyl 4-chloro-3-oxobutyrate represented by the formula (3) below:

[Chemical formula 12]

(3)

2-chloro-1-(3'-chlorophenyl)ethanone represented by the formula (5) below:

[Chemical formula 13]

(5)

and tert-butyl (S)-6-benzoyloxy-5-hydroxy-3-oxohexanoate represented by the formula (7) below:

[Chemical formula 14]

(7)

However, the compound containing a carbonyl group is not particularly limited as long as it can be reduced in the aforementioned reaction conditions and converted into an optically active alcohol.

In the aforementioned reaction conditions, when 3-oxo-3-phenylpropanenitrile represented by the formula (1) above is used as a substrate, (R)-3-hydroxy-3-phenylpropenenitrile represented by the formula (2) below:

[Chemical formula 15]

(2)

can be obtained.

When ethyl 4-chloro-3-oxobutyrate represented by the formula (3) above is used as a substrate, ethyl (S)-4-chloro-3-hydroxybutyrate represented by the formula (4) below:

[Chemical formula 16]

(4)

can be obtained.

When 2-chloro-1-(3'-chlorophenyl)ethanone represented by the formula (5) above is used as a substrate, (R)-2-chloro-1-(3'-chlorophenyl)ethanol represented by the formula (6) below:

[Chemical formula 17]

(6)

can be obtained.

Furthermore, when tert-butyl (S)-6-benzoyloxy-5-hydroxy-3-oxohexanoate represented by the formula (7) above is used as a substrate, tert-butyl (3R,5S)-6-benzoyloxy-3,5-dihydroxyhexanoate represented by the formula (8) below:

[Chemical formula 18]

(8)

can be obtained.

11. Purification and Analysis

An optically active alcohol produced by the reaction can be purified by a conventional method, for example, by extracting a reaction solution containing an optically active alcohol produced by the reaction with an organic solvent such as ethyl acetate and toluene, removing the organic solvent by distillation under reduced pressure, and subjecting the resultant mixture to distillation, recrystallization or chromatographic process.

The amounts of 3-oxo-3-phenylpropanenitrile and (R)-3-hydroxy-3-phenylpropanenitrile and the optical purity of (R)-3-hydroxy-3-phenylpropanenitrile can be obtained by capillary gas chromatography (column: CHIRALDEX G-TA (IDO, 25 mm×20 m: manufactured by Tokyo Chemical Industry Co., Ltd.,), column temperature: 130° C., carrier gas: helium (150 kPa). detection: FID).

The amounts of ethyl 4-chloro-3-oxobutyrate and ethyl (S)-4-chloro-3-hydroxybutyrate can be obtained by gas chromatography (column: PEG-20M, Chromosorb WAW DMCS 10% 80/100 mesh (ID 3-mm×1 m; manufactured by G-L Sciences), column temperature: 150° C., carrier gas: nitrogen, detection: FID). Furthermore, the optical purity of ethyl (S)-4-chloro-3-hydroxybutyrate is measured by high performance liquid chromatography (column: Chiralcel OB (ID 4.6 mm×250 mm; manufactured by Daicel Chemical Industries Ltd.), eluent: n-hexane/isopropanol=9/1, flow rate: 0.8 ml/min, detection: 215 nm, column temperature: room temperature).

The amounts of 2-chloro-1-(3'-chlorophenyl)ethanone and (R)-2-chloro-1-(3'-chlorophenyl)ethanol can be obtained by high performance liquid chromatography (column: YMC-Pack ODS A-303 (ID 4.6 mm×250 mm), manufactured by YMC, eluent: water/acetonitrile=1/1, flow rate: 1 ml/min, detection: 210 nm, column temperature: room temperature). Furthermore, the optical purity of (R)-2-chloro-1-(3-'-chlorophenyl)ethanol can be measured by high performance liquid chromatography (column: Chiralcel OJ (ID 4.6 mm×250 mm; manufactured by Daicel Chemical Industries Ltd.), eluent: n-hexane/isopropanol=39/1, flow rate: 1 ml/min, detection: 254 nm, column temperature: room temperature).

The amounts of tert-butyl (S)-6-benzoyloxy-5-hydroxy-3-oxohexanoate and tert-butyl (3R,5S)-6-benzoyloxy-3,5-dihydroxyhexanoate and furthermore, the diastereomer excess ratio of tert-butyl (3R,5S)-6-benzoyloxy-3,5-dihydroxyhexanoate can be obtained by high performance liquid chromatography (column: YMC-Pack ODS A-303 (ID 4.6 mm×250 mm), manufactured by YMC, eluent: water/acetonitrile=1/1, flow rate: 1 ml/min, detection: 210 nm, column temperature: room temperature).

As described in the foregoing, according to the present invention, the polypeptide of the present invention can be efficiently produced and a process for producing a useful and optically active alcohol represented by (R)-3-hydroxy-3-phenylpropanenitrile can be provided by use of the polypeptide.

EXAMPLES

The present invention will be more specifically described by way of Examples below, which will not be construed as limiting the invention. Note that specific manipulation methods regarding recombinant DNA techniques used in the following Examples are described in the following publications:
Molecular Cloning 2nd Edition (Cold Spring Harbor Laboratory Press, 1989),
Current Protocols in Molecular Biology (Greene Publishing Associates and Wiley-Interscience).

Example 1

Purification of Polypeptide

In accordance with the following method, a polypeptide from *Candida magnoliae* strain NBRC0661, having an activity of asymmetrically reducing 3-oxo-3-phenylpropanenitrile to produce (R)-3-hydroxy-3-phenylpropanenitrile was separated and purified as a single product. Purification operation was performed at 4° C. unless otherwise specified.

The reduction activity to 3-oxo-3-phenylpropanenitrile was obtained by dissolving a substrate, 3-oxo-3-phenylpropanenitrile so as to have a final concentration of 0.5 mM and a coenzyme NADPH in a final concentration of 0.25 mM in a 100 mM phosphate buffer (pH 6.5) containing 0.33% (v/v) of dimethylsulfoxide, further adding a crude enzyme solution, reacting the mixture at 30° C. for one minute, measuring absorbance of the reaction solution at a wavelength of 340 nm, and calculating a reduction rate of the absorbance. In the reaction conditions, the activity of oxidizing 1 μmol of NADPH to NADP per minute was defined as 1 unit.

(Culturing of Microorganism)

In a 30 L jar fermentor (manufactured by B. E. Marubishi Co. Ltd.), 18 L of liquid medium was prepared containing 4% of glucose, 0.3% of yeast extract, 0.7% of potassium dihydrogenphosphate, 1.3% of diammonium hydrogen phosphate, 0.1% of sodium chloride, 0.08% of magnesium sulfate 7-hydrate, 0.006% of zinc sulfate 7-hydrate, 0.009% of ferrous sulfate 7-hydrate, 0.0005% of copper sulfate 5-hydrate, 0.001% of mangan sulfate 4-6 hydrate, and 0.01% of Adecanol LG-109 (manufactured by NFO corporation). The liquid medium was sterilized by vapor at 120° C. for 20 minutes.

To this medium, 180 ml of a culture solution of *Candida magnoliae* strain NBRC0661 previously cultured in the same type of medium was inoculated. The culture medium was cultured with stirring at a rotation rate of 250 rpm and supplying air at a rate of 5.0 NL/min at 30° C. and while adjusting the lower pH value to 5.5 by adding a 30% (w/w) aqueous sodium hydroxide solution dropwise. Culturing was performed for 30 hours, while adding 655 g of a 55% (w/w) aqueous glucose solution each of 18 hours, 22 hours and 26 hours after initiation of culturing.

(Preparation of Cell-Free Extraction)

Bacterial cells were centrifugally collected from the culture solution above and washed with a 0.8% aqueous sodium chloride solution. The bacterial cells were suspended in a 100 mM phosphate buffer (pH 7.0) containing 5 mM of β-mercaptoethanol and 0.1 mM phenyl methane sulfonyl fluoride and disrupted by a Dyno-mill (manufactured by Willy A. Bachofen AG.). Thereafter, cell residues were centrifugally removed from the disrupted material to obtain 1900 ml of a cell-free extract.

(Removal of Nucleic Acid)

To the cell-free extract obtained above, 100 ml of a 5% aqueous protamine sulfate solution was added. The mixture was stirred overnight and centrifuged to remove a precipitate.

(Fractionation with Ammonium Sulfate)

After nucleic acids were removed in the above, the pH of the crude enzyme solution was adjusted to 7.0 by ammonia water. While maintaining the pH, ammonium sulfate was added and dissolved so as to obtain 50% saturation. The precipitate generated was centrifugally removed. To the supernatant, ammonium sulfate was further added and dissolved so as to obtain 60% saturation while maintaining the pH to 7.0 in the same manner as above. The generated precipitate was centrifugally collected. The precipitate was dissolved in a 10 mM phosphate buffer (pH 7.0) and dialyzed against the same buffer overnight to obtain active fractions.

(DEAE TOYOPEARL Column Chromatography)

The active fractions obtained by fractionation with ammonium sulfate were loaded to a DEAE-TOYOPEARL 650M column (400 ml, manufactured by TOSOH Corporation), which was previously equilibrated with a 10 mM phosphate buffer (pH 7.0) to adsorb the active fractions. After the column was washed with the same buffer, the active fractions were eluted by linear gradient with NaCl (0 M to 0.5 M). The active fractions were collected and dialyzed against a 10 mM phosphate buffer (pH 7.0) overnight.

(Blue Sepharose Column Chromatography)

The active fractions obtained by DEAE-TOYOPEARL column chromatography were loaded to Blue Sepharose CL-6B column (50 ml, manufactured by Amersham Biosciences), which was previously equilibrated with a 10 mM phosphate buffer (pH 7.0) to adsorb the active fractions. After the column was washed with the same buffer, the active fractions were eluted by linear gradient with NaCl (0 M to 1 M). The active fractions were collected and dialyzed against a 10 mM phosphate buffer (pH 7.0) overnight.

(2',5'-ADP Sepharose Column Chromatography)

The active fractions obtained by Blue sepharose column chromatography were loaded to 2',5'-ADP sepharose column (20 ml, manufactured by Amersham Biosciences), which was previously equilibrated with a 10 mM phosphate buffer (pH 7.0) to adsorb the active fractions. After the column was washed with the same buffer, the active fractions were eluted by linear gradient with NaCl (0 M to 1 M). The active fractions were collected and dialyzed against a 10 mM phosphate buffer (pH 7.0) overnight.

(HiTrap Phenyl HP Column Chromatography)

To the active fractions obtained by 2',5'-ADP sepharose column chromatography, ammonium sulfate was added so as to obtain a final concentration of 35%. The mixture was loaded to a HiTrap Phenyl HP column (manufactured by Amersham Biosciences), which was previously equilibrated with a 10 mM phosphate buffer (pH 7.0) containing 35% ammonium sulfate, to adsorb the active fractions. After the column was washed with the same buffer, the active fractions were eluted by linear gradient with NaCl (35% to 0%). The active fractions were collected and dialyzed against a 10 mM phosphate buffer (pH 7.0) overnight to obtain a purified polypeptide sample.

Example 2

Gene Cloning (Preparation of PCR Primer)

The purified polypeptide obtained in Example 1 was denatured in the presence of 8M urea, and thereafter digested with lysyl end-peptidase (manufactured by Wako Pure Chemical Industries Ltd.) derived from *Achromobacter*. The amino acid sequences of the obtained peptide fragments were determined by an ABI492-type protein sequencer (manufactured by PerkinElmer). Based on the putative DNA sequence from the amino acid sequence, a primer 1:5'-cargarcaytaygtntggcc-3' (SEQ ID NO: 3 of the sequence listing) and primer 2: 5'-atygcrtcnggrtadatcca-3' (SEQ ID NO: 4 of the sequence listing) were synthesized for amplifying a part of the gene encoding the polypeptide by PCR.

(PCR Amplification of Gene)

Chromosomal DNA was extracted from bacterial cells of *Candida magnoliae* strain NBRC0661 cultured in the same manner as in Example 1 in accordance with the method of Visser et al. (Appl. Microbiol. Biotechnol., 53, 415 (2000)). Subsequently, PCR was performed using the DNA primers 1 and 2 prepared above, and the chromosomal DNA thus obtained as a template. As a result, a DNA fragment of about 0.5 kbp, which was conceivably a part of the desired gene, was amplified. PCR was performed by using TaKaR Ex Taq (manufactured by Takara Bio Inc.) as DNA polymerase under reaction conditions according to the instructions. The DNA fragment was cloned to plasmid pT7Blue T-Vector (manufactured by Novagen) and the base sequence thereof was analyzed by use of ABI PRISM Dye Terminator Cycle Sequencing Ready Reaction Kit (manufactured by PerkinElmer) and an ABI 373A DNA Sequencer (manufactured by PerkinElmer). The resultant base sequence is shown in SEQ ID NO: 5 of the sequence listing.

(Determination of the Entire Sequence of Desired Gene by i-PCR Method)

The chromosomal DNA of *Candida magnoliae* strain NBRC0661 prepared above was completely digested with restriction enzyme PstI. A mixture of the obtained DNA fragments was treated with T4 ligase to form intramolecular cyclization. Using this as a template, i-PCR method (Nucl. Acids Res., 16, 8186 (1988)) was performed. In this manner, the entire base sequence of a gene containing the base sequence represented by SEQ ID NO: 5 above. The results are shown in SEQ ID NO: 1 of the sequence listing. The aforementioned i-PCR was performed using TaKaRa LA Taq (Takara Bio. Inc.) as DNA polymerase under the reaction conditions according to the instructions. The amino acid sequence encoded by the base sequence represented by SEQ ID NO: 1 is shown in SEQ ID NO: 2.

Example 3

Construction of Expression Vector

PCR was performed using primer 3: 5'-gtgcatatgtcttctct-tcacgctcttg-3'(SEQ ID NO: 6 of the sequence listing) and primer 4: 5'-ggcgaattcttattaaacggtagagccattgtcg-3'(SEQ ID NO: 7 of the sequence listing), and chromosomal DNA of *Candida magnoliae* strain NBRC0661 obtained in Example 2 as a template. As a result, a double stranded DNA was obtained having an NdeI recognition site added to the portion of the initiation codon of a gene consisting of the base sequence represented by SEQ ID NO: 1 of the sequence listing and an EcoRI recognition site added immediately after the termination codon. PCR was performed using TaKaRa LA Taq (manufactured by Takara Bio Inc.) as DNA polymerase under the reaction conditions according to the instructions. The DNA was digested with NdeI and EcoRI and inserted between the NdeI recognition site and the EcoRI recognition site downstream of the lac promoter of plasmid pUCNT (U.S. Pat. No. 6,083,752). In this manner, a recombination vector pNTCM was constructed.

Example 4

Construction of Expression Vector Further Containing Glucose Dehydrogenase Gene

PCR was performed using primer 5: 5'-gccgaattctaaggag-gttaacaatgtataaa-3'(SEQ ID NO: 8 of the sequence listing) and primer 6: 5'-gcggtcgacttatccgcgtcctgcttgg-3'(SEQ ID NO: 9 of the sequence listing), and plasmid pGDK1 (Eur. J. Biochem., 186, 389 (1989)) as a template. As a result, a double stranded DNA was obtained in which a ribosome connecting sequence of *E. coli* was added to a position by 5 bases upstream of the initiation codon of a glucose dehydrogenase gene (hereinafter referred to as "GDH") derived from *Bacillus megaterium* strain LAM1030, further an EcoRI cleaving site was added to the site immediately therebefore, and an SalI cleaving site was added to immediately after the termination codon. The DNA fragment thus obtained was digested with EcoRI and SalI and inserted between the EcoRI recognition site and the SalI recognition site downstream of the lac promoter of plasmid pUCNT (U.S. Pat. No. 6,083, 752). In this manner, a recombination vector pNTG1 was constructed.

Figure 1:
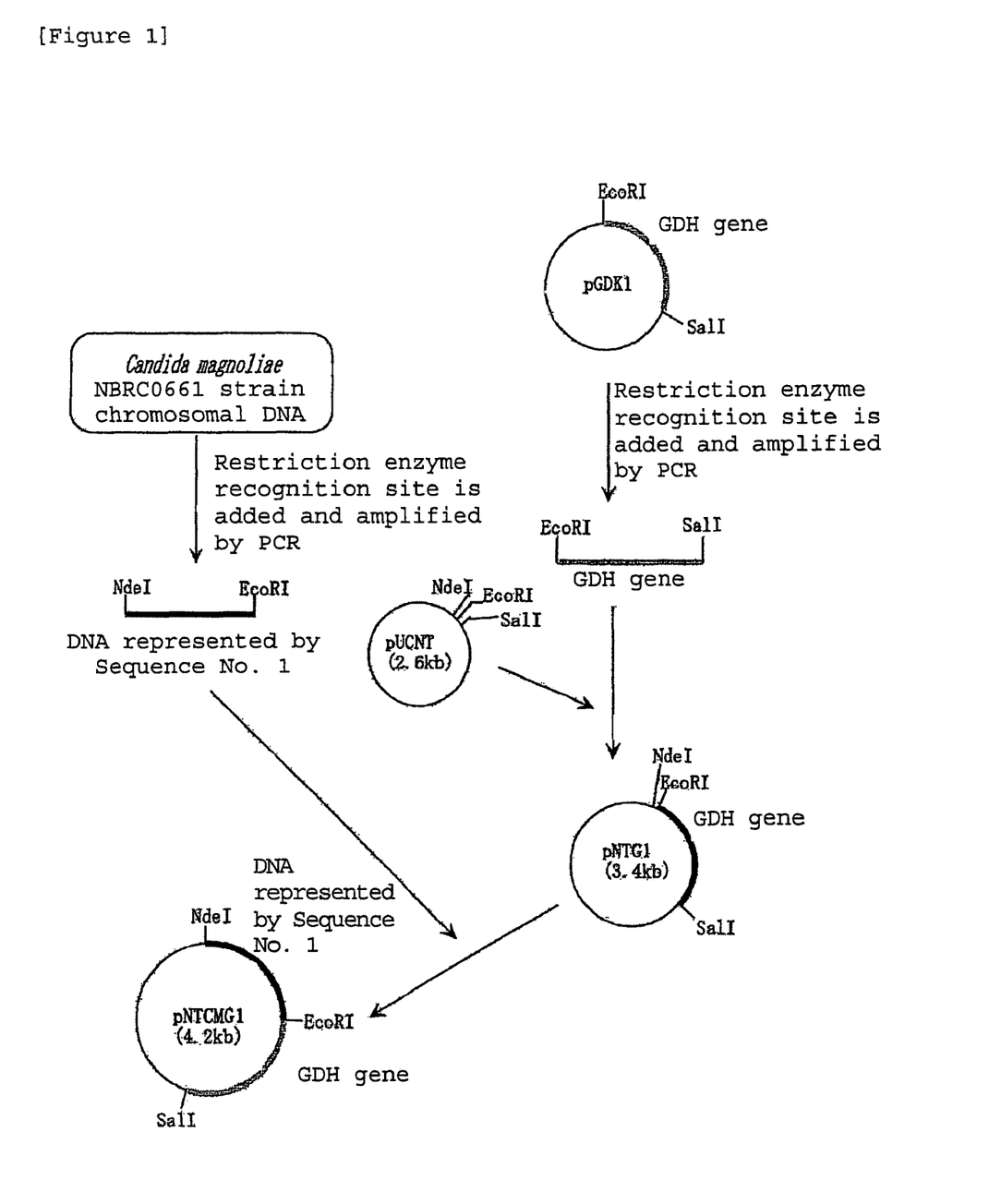
FIG. 1 shows the method and structure of a recombinant vector pNTCMG1.

Subsequently, a double stranded DNA was prepared having an NdeI recognition site added to the portion of the initiation codon of a gene consisting of the base sequence represented by SEQ ID NO: 1 of the sequence listing and an EcoRI recognition site added to the portion immediately after the termination codon, in the same manner as in Example 3. The resultant DNA was inserted between the NdeI recognition site and the EcoRI recognition site of the recombinant vector pNTG1 mentioned above. In this manner, a recombinant plasmid pNTCMG1 was constructed. The preparation method and structure of pNTCMG1 are shown in FIG. 1.

Example 5

Preparation of Transformant

Using the recombinant vector pNTCM constructed in Example 3, the *E. coli* HB101 competent cell (manufactured by Takara Bio Inc.) was transformed to obtain *E. coli* HB101 (pNTCM). This transformant has been deposited as of Sep. 26, 2005 under the accession number of FERM BP-10418 at an independent organization, the International Patent Organism Depositary of the National Institute of Advanced Industrial Science and Technology (located at Tsukuba Central 6, 1-1-1 Higashi, Tsukuba, Ibaraki, 305-8566, Japan). Note that the original national deposition date of Oct. 23, 2003 for the strain has been transferred to international deposition based on the Budapest Treaty.

Similarly, the *E. coli* HB101 competent cell (manufactured by Takara Bio Inc.) was transformed with the recombinant vector pNTCMG1 constructed in Example 4 to obtain *E. coli* HB101 (pNTCMG1).

Example 6

Expression of Gene in Transformant

Two types of transformants obtained in Example 5, and *E. coli* HB101 (pUCNT), which is a transformant containing a vector plasmid pUCNT, were separately inoculated in 50 ml of 2×YT medium (1.6% of tryptone, 1.0% of yeast extract, 0.5% of NaCl, pH 7.0) containing 200 µg/ml ampicillin and cultured while shaking at 37° C. for 24 hours. Bacterial cells were centrifugally collected and suspended in 50 ml of 100 mM phosphate buffer (pH 6.5). The suspended bacterial cells were disrupted by an UH-50 type ultrasonic homogenizer (manufactured by SMT) and thereafter bacterial debris was centrifugally removed to obtain a cell-free extract. The reduction activity to 3-oxo-3-phenylpropanenitrile and GDH activity of the cell-free extract were measured and expressed as relative activities in Table 1. In each of the two types of transformants obtained in Example 5, the reduction activity to 3-oxo-3-phenylpropanenitrile was observed. Furthermore, the expression of the GDH activity was observed in *E. coli* HB101 (pNTCMG1) containing a GDH gene. The reduction activity to 3-oxo-3-phenylpropanenitrile was measured by the method described in Example 1. The GDH activity was obtained by adding 0.1 M glucose, 2 mM coenzyme NADP and a crude enzyme solution to 1M tris hydrochloride buffer (pH 8.0), performing a reaction at 25° C. for one minute, measuring absorbance at a wave length of 340 nm, calculating an increasing rate of the absorbance. The enzymatic activity for reducing 1 μmol of NADP to NADPH per minute in the reaction conditions was defined as 1 unit. The protein concentration of the cell-free extract was measured by a protein assay kit (manufactured by BIO-RAD).

TABLE 1

| Name of bacterial strain | Relative RRG activity (U/mg) | Relative GDH activity (U/mg) |
| --- | --- | --- |
| E. coli HB101 (pUCNT) | <0.01 | <0.01 |
| E. coli HB101 (pNTCM) | 0.22 | <0.01 |
| E. coli HB101 (pNTCMG1) | 0.13 | 269 |

Example 7

Production of (R)-3-hydroxy-3-phenylpropanenitrile Using Transformant

To 50 ml of the cell-free extract of E. coli HB101 (pNTCM) prepared in the same manner as in Example 6, 2000U of glucose dehydrogenase (manufactured by Amano Enzyme Inc.), 3 g of glucose, 6 mg of NADP and 2 g of 3-oxo-3-phenylpropanenitrile were added. The mixture was stirred at 30° C. for 22 hours while adjusting the pH of the mixture to 6.5 by adding 5 M sodium hydroxide dropwise. After completion of the reaction, extraction was performed with ethyl acetate. The solvent was removed and then an extracted material was analyzed. As a result, (R)-3-hydroxy-3-phenylpropanenitrile having an optical purity of 97.3% e.e. was obtained in a yield of 86.3%.

The amounts of 3-oxo-3-phenylpropanenitrile and (R)-3-hydroxy-3-phenylpropanenitrile and the optical purity of (R)-3-hydroxy-3-phenylpropanenitrile were obtained by capillary gas chromatography (column: CHIRALDEX G-TA manufactured by Tokyo Chemical Industry Co., Ltd., φ0.25 mm×20 m, column temperature: 130° C., carrier gas: helium (150 kPa), detection: FID).

Example 8

Production of (R)-3-hydroxy-3-phenylpropanenitrile Using Transformant

To 50 ml of the cell-free extract of E. coli HB101 (pNTCMG1) prepared in the same manner as in Example 6, 3 g of glucose, 6 mg of NADP and 2 g of 3-oxo-3-phenylpropanenitrile were added. The mixture was stirred at 30° C. for 22 hours while adjusting the pH of the mixture to 6.5 by adding 5 M sodium hydroxide dropwise. After completion of the reaction, extraction was performed with ethyl acetate. The solvent was removed and then an extracted material was analyzed. As a result, (R)-3-hydroxy-3-phenylpropanenitrile having an optical purity of 97.4% e.e. was obtained in a yield of 92.1%.

The amounts of 3-oxo-3-phenylpropanenitrile and (R)-3-hydroxy-3-phenylpropanenitrile and the optical purity of (R)-3-hydroxy-3-phenylpropanenitrile were obtained in the same manner as in Example 7.

Production of (R)-2-chloro-1-(3'-chlorophenyl)ethanol Using Transformant

To 50 ml of a culture solution of E. coli HB101 (pNTCMG1) prepared in the same manner as in Example 6, 5 g of glucose, 6 mg of NADP, 4 g of 2-chloro-1-(3'-chlorophenyl)ethanone and 4 g of toluene were added. The mixture was stirred at 30° C. for 24 hours while adjusting the pH of the mixture to 6.5 by adding 5 M sodium hydroxide dropwise. After completion of the reaction, the reaction solution was extracted with toluene. The solvent was removed and then an extracted material was analyzed. As a result, (R)-2-chloro-1-(3'-chlorophenyl)ethanol having an optical purity of 82.0% e.e. was obtained in a yield of 90.5%.

The amounts of 2-chloro-1-(3'-chlorophenyl)ethanone and (R)-2-chloro-1-(3'-chlorophenyl)ethanol were obtained by high performance liquid chromatography (column: YMC-Pack ODS A-303 (ID 4.6 mm×250 mm), manufactured by YMC, eluent: water/acetonitrile=1/1, flow rate: 1 ml/min, detection: 210 nm, column temperature: room temperature). Furthermore, the optical purity of (R)-2-chloro-1-(3'-chlorophenyl)ethanol was measured by high performance liquid chromatography (column: Chiralcel OJ (ID 4.6 mm×250 mm; manufactured by Daicel Chemical Industries Ltd., eluent: n-hexane/isopropanol=39/1, flow rate: 1 ml/min, detection: 254 nm, column temperature: room temperature).

Example 10

Production of ethyl (S)-4-chloro-3-hydroxybutyrate Using Transformant

To 50 ml of a culture solution of E. coli HB101 (pNTCMG1) prepared in the same manner as in Example 6, 6 g of glucose, 4 mg of NADP were added. The reaction solution was stirred at 30° C. While the pH of the reaction solution was adjusted to pH 6.5 by adding 5 M sodium hydroxide dropwise, 5 g in total of ethyl 4-chloro-3-oxobutyrate was added at a rate of 0.5 g/hour. Stirring was continued for a further 5 hours. After completion of the reaction, the reaction solution was extracted with ethyl acetate. The solvent was removed and then an extracted material was analyzed. As a result, ethyl (S)-4-chloro-3-hydroxybutyrate having an optical purity of 80.5% e.e. was obtained in a yield of 93.1%.

The amounts of ethyl 4-chloro-3-oxobutyrate and ethyl (S)-4-chloro-3-hydroxybutyrate were obtained by gas chromatography (column: PEG-20M, Chromosorb WAW DMCS 10% 80/100 mesh (ID 3 mm×1 m; manufactured by G-L Sciences), column temperature: 150° C., carrier gas: nitrogen, detection: FID). Furthermore, the optical purity of ethyl (S)-4-chloro-3-hydroxybutyrate is obtained by high performance liquid chromatography (column: Chiralcel OB (ID 4.6 mm×250 mm; manufactured by Daicel Chemical Industries Ltd.), eluent: n-hexane/isopropanol=9/1, flow rate: 0.8 ml/min, detection: 215 nm, column temperature: room temperature).

Example 11

Production of tert-butyl 6-benzoyloxy-3,5-dihydroxyhexanoate Using Transformant

To 40 ml of a culture solution of E. coli HB101 (pNTCMG1) prepared in the same manner as in Example 6, 3 g of glucose, 6 mg of NADP, 4 g of tert-butyl (S)-6-benzoyloxy-5-hydroxy-3-oxohexanoate and 1.6 g of toluene were added. The reaction solution was stirred at 30° C. for 24 hours while adjusting the pH of the reaction solution to pH 6.5 by adding 5 M sodium hydroxide dropwise. After completion of the reaction, the reaction solution was extracted with toluene. The solvent was removed and then an extracted material was analyzed. As a result, tert-butyl (3R,5R)-6-benzoyloxy-3,5-dihydroxyhexanoate having an excess rate of a diastereomer of 99.7% d.e. was obtained in a yield of 92.3%.

The amounts of tert-butyl (S)-6-benzoyloxy-5-hydroxy-3-oxohexanoate and tert-butyl (3R,5R)-6-benzyloxy-3,5-dihydroxyhexanoate and further the excessive rate of a diastereomer of tert-butyl (3R,5R)-6-benzyloxy-3,5-dihydroxyhexanoate were obtained by high performance liquid chromatography (column: YMC-Pack ODS A-303 (ID 4.6 mm×250 mm), manufactured by YMC, eluent: water/ acetonitrile=1/1, flow rate: 1 ml/min, detection: 210 nm, column temperature: room temperature).

Example 12

Substrate Specificity of Polypeptide

To 100 mM phosphate buffer (pH 6.5) containing 0.33% (v/v) dimethylsulfoxide, a substrate, a carbonyl compound serving as a substrate was dissolved so as to obtain a final concentration of 1 mM and a coenzyme NADPH in a final concentration of 0.25 mM. To the mixture, the purified polypeptide prepared in Example 1 was added in an appropriate amount and a reaction was performed at 30° C. for one minute. Based on a reduction rate of absorbance of the reaction solution at a wavelength of 340 nm, the reduction activity to each carbonyl compound was calculated. This was expressed by a relative value to the activity to 3-oxo-3-phenylpropanenitrile as being in Table 2. As is apparent from Table 2, the polypeptide of the present invention exhibits reduction activity to a wide variety of carbonyl compounds.

TABLE 2

| Substrate specificity of polypeptide | |
|---|---|
| Reaction substrate | Relative activity (%) |
| 3-oxo-3-phenylpropanenitrile | 100 |
| 2-acetylpyridine | 1926 |
| 3-acetylpyridine | 2107 |
| 4-acetylpyridine | 15710 |
| acetophenone | 1023 |
| m-nitroacetophenone | 5056 |
| p-chloroacetophenone | 2347 |
| p-fluoroacetophenone | 722 |
| 3,4-dimethoxyacetophenone | 2889 |
| p-methylacetophenone | 542 |
| 2-hydroxyacetophenone | 1806 |
| 2-chloro-1-(3'-chlorophenyl)ethanone | 10473 |
| 1-phenyl-2-butanone | 1144 |
| propiophenone | 3010 |
| benzylacetone | 241 |
| ethyl benzoylacetate | 7704 |
| 2-butanone | 181 |
| 2-hexanone | 602 |
| 2-heptanone | 782 |
| chloroacetone | 2468 |
| hydroxyacetone | 361 |
| 4-hydroxy-2-butanone | 301 |
| 4-methyl-2-pentanone | 60 |
| cyclopropyl methyl ketone | 181 |
| methyl pyruvate | 9450 |
| ethyl acetoacetate | 903 |
| benzyl acetoacetate | 4936 |
| ethyl 4-chloroacetoacetate | 8547 |
| 2-keto-n-butyric acid | 1866 |
| oxalacetic acid | 421 |

[Sequence Listing]

The invention claimed is:

1. An isolated DNA selected from the group consisting of:
   (a) an isolated DNA comprising the polynucleotide sequence of SEQ ID NO: 1; and
   (b) an isolated DNA that encodes a polypeptide with at least 90% amino acid sequence identity to SEQ ID NO: 2, and wherein said polypeptide has an activity of asymmetrically reducing 3-oxo-3-phenylpropanenitrile represented by the formula (1) below;

(1)

to produce (R)-3-hydroxy-3-hydroxy-3-phenylpropanenitrile represented by the formula (2) below;

(2)

2. An isolated DNA encoding a polypeptide consisting of the amino acid sequence of SEQ ID NO: 2.

3. A vector comprising the DNA according to claim 1.

4. The vector according to claim 3, wherein said vector is plasmid pNTCM.

5. The vector according to claim 3, wherein said vector further comprises a polynucleotide sequence encoding a polypeptide having glucose dehydrogenase activity.

6. The vector according to claim 5, wherein the polypeptide having glucose dehydrogenase activity is a glucose dehydrogenase derived from *Bacillus megaterium*.

7. A transformed microbial cell obtained by transforming a microbial host cell with the DNA according to claim 1 or the vector according to claim 3.

8. The transformed microbial cell according to claim 7, wherein the host cell is *Escherichia coli*.

9. The transformed microbial cell according to claim 8, wherein said transformed microbial cell is *Escherichia coli* HB101(pNTCM) FERM BP-10418.

10. The transformed microbial cell according to claim 7, wherein said transformed microbial cell further comprises a polynucleotide encoding a polypeptide having glucose dehydrogenase activity.

11. A process for producing an optically active alcohol selected from the group consisting of (R)-3-hydroxy-3-phenylpropanenitrile represented by the following formula (2), (S)-4-chloro-3-hydroxybutyrate represented by the following formula (4), (R)-2-chloro-1-(3'-chlorophenyl)ethanol represented by the following formula (6) and tert-butyl (3R,5S)-6-benzoyloxy-3,5-dihydroxyhexanoate represented by the following formula (8):

(2)

(4)

(6)

(8)

comprising the steps of:
(a) reacting the transformed microbial host cell according to claim 9 with a corresponding carbonyl compound selected from the group consisting of 3-oxo-3-phenylpropanenitrile represented by the following formula (1), ethyl 4-chloro-3-oxobutyrate represented by the following formula (3), 2-chloro-1-(3'-chlorophenyl)ethanone represented by the following formula (5) and tert-butyl (S)-6-benzoyloxy-5-hydroxy-3-oxohexanoate represented by the following formula (7)

(1)

(3)

(5)

(7)

and;
(b) isolating the optically active alcohol of Formula (2), (4), (6) or (8) produced in step (a).

* * * * *